United States Patent
Billard

(10) Patent No.: US 10,828,488 B2
(45) Date of Patent: Nov. 10, 2020

(54) PROBING DEVICE FOR MANAGING STRESS URINARY INCONTINENCE

(71) Applicant: AKSE, Moissy-Cramayel (FR)

(72) Inventor: Georges Billard, Perols (FR)

(73) Assignee: AKSE, Moissy-Cramayel (FR)

( * ) Notice: Subject to any disclaimer, the term of this patent is extended or adjusted under 35 U.S.C. 154(b) by 72 days.

(21) Appl. No.: 15/744,949

(22) PCT Filed: Jul. 15, 2016

(86) PCT No.: PCT/FR2016/051824
§ 371 (c)(1),
(2) Date: Jan. 15, 2018

(87) PCT Pub. No.: WO2017/009584
PCT Pub. Date: Jan. 19, 2017

(65) Prior Publication Data
US 2018/0264259 A1    Sep. 20, 2018

(30) Foreign Application Priority Data

Jul. 15, 2015 (FR) .................................. 15 56685
Apr. 6, 2016 (FR) .................................. 16 53023

(51) Int. Cl.
| | |
|---|---|
| *A61N 1/36* | (2006.01) |
| *A61N 1/05* | (2006.01) |
| *A61B 5/0488* | (2006.01) |
| *A61B 5/20* | (2006.01) |
| *A61B 5/22* | (2006.01) |
| *A63B 23/20* | (2006.01) |

(52) U.S. Cl.
CPC ...... *A61N 1/36007* (2013.01); *A61B 5/04882* (2013.01); *A61B 5/202* (2013.01); *A61N 1/0512* (2013.01); *A61N 1/0524* (2013.01); *A61B 5/205* (2013.01); *A61B 5/227* (2013.01); *A63B 23/20* (2013.01)

(58) Field of Classification Search
CPC .............. A61N 1/36007; A61N 1/0512; A61N 1/0524; A61B 5/04882; A61B 5/202; A63B 23/20
See application file for complete search history.

(56) References Cited

U.S. PATENT DOCUMENTS

| | | | | |
|---|---|---|---|---|
| 4,515,167 | A * | 5/1985 | Hochman | .......... A61B 10/0012 600/549 |
| 2003/0083590 | A1* | 5/2003 | Hochman | ............ A61B 5/0002 600/549 |
| 2009/0222058 | A1* | 9/2009 | Craggs | ................. A61N 1/0512 607/41 |

FOREIGN PATENT DOCUMENTS

| | | |
|---|---|---|
| EP | 0 638 329 A1 | 2/1995 |
| FR | 2827520 A1 | 1/2003 |
| FR | 2930713 A1 | 11/2009 |

* cited by examiner

*Primary Examiner* — George R Evanisko
(74) *Attorney, Agent, or Firm* — Craft Chu PLLC; Andrew W. Chu

(57) ABSTRACT

The self-contained endocavitary probe device for managing stress incontinence is capable of being inserted into the vaginal or rectal cavity of a person. The device includes at least one self-contained electrical power supply so as to supply power to at least one device for measuring the variation in a parameter resulting from physical stress and to at least one electrical muscle stimulation device in contact with at least one muscle capable of maintaining urinary (Continued)

continence. The electrical stimulation device is activated in the event of variation in the parameter.

6 Claims, 1 Drawing Sheet

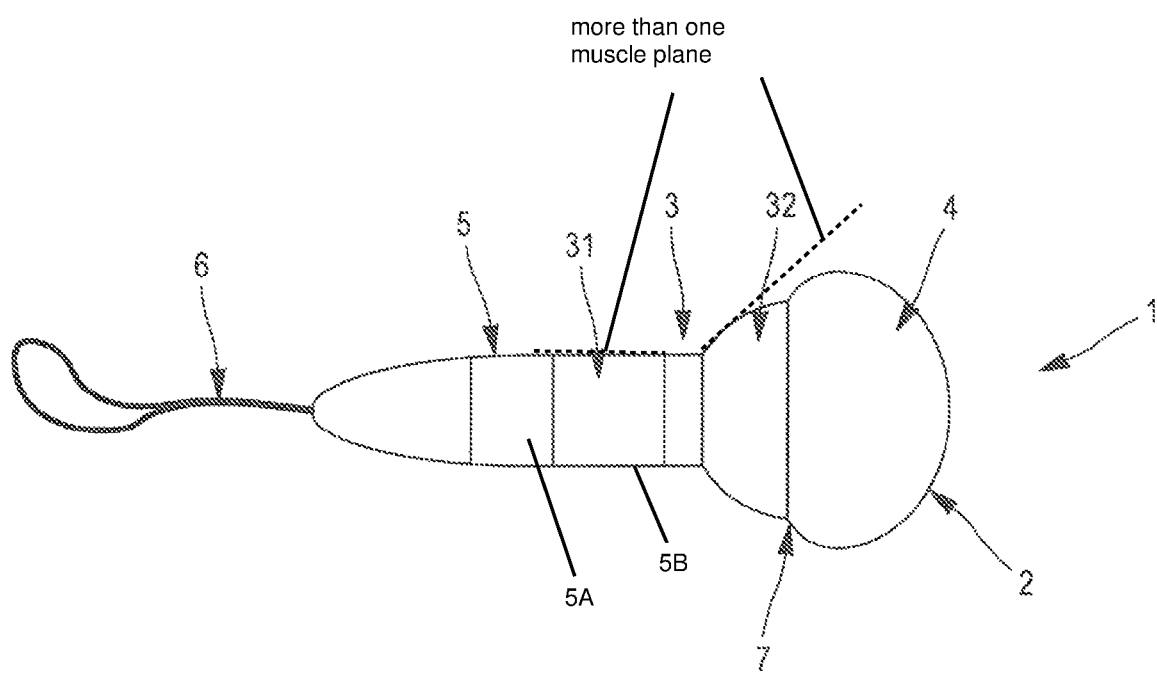

PROBING DEVICE FOR MANAGING STRESS URINARY INCONTINENCE

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to the field of the management of the incontinence under stress, and in particular, but not exclusively, of the urinary incontinence.

The invention more particularly relates to an innovative device permitting to permanently avoid urinary incontinence under stress, also known as stress urinary incontinence.

There are different types of urinary incontinence, all characterized by an involuntary loss of urine through the outlet channel of the bladder, the urethra.

As regards the urinary incontinence under stress, it is more particularly characterized by an involuntary loss of urine via the urethra following a physical effort, in particular a coughing fit, sneezing, laughter or a lifting of a more or less heavy load.

This physical effort, irrespective of its nature, will cause an increase of the pressure at the level of the abdominal area. The abdominal pressure is then naturally transferred onto the bladder. When the muscles of the perineum and the urinary sphincter do not function enough to counteract this increase in pressure and to maintain the bladder closed, a flow of urine, scanty and as a jet, is likely to occur, and this without feeling a need felt in advance.

Beyond the embarrassment, even the shame, felt by the person with urinary incontinence, this disorder can cause more serious repercussions, namely at psychological or hygienic level. In addition, urinary incontinence can cause skin irritation.

2. Description of Related Art Including Information Disclosed Under 37 CFR 1.97 and 37 CFR 1.98

Traditionally, the diagnosis of urinary incontinence is made following a simple interrogation of the person. In this way, the specialist will namely try to find antecedents, in particular obstetric and pelvic surgery antecedents.

It has also been provided, for several decades, to diagnose a problem of incontinence by performing a urodynamic exploration during which the evolution of the pressures in the bladder and in the rectum will be measured, following the application of determined stimuli mimicking the conditions in which the urinary leakage occurs.

This urodynamic exploration is performed by means of a probe inserted into the bladder via the urethra, said probe being connected, via a wired link, to means for stimulating (bladder filling) and recording a response, these means being particularly impressive and positioned outside the body of the patient.

Once the diagnosis of urinary incontinence under stress is made, there are, in the state of the art, various solutions that are provided to the persons suffering from this discomfort.

For women suffering from stress incontinence are often provided, as first line, perineal reeducation sessions in particular aimed at gaining muscle strength in the pelvis and at more effectively controlling the functions of the muscles of the perineum, in order to also improve the control of the bladder and the closing pressure of the urethra.

The existing methods are multiple, and namely biofeedback and electrostimulation are applied, which facilitate the execution of the exercises of the pelvic floor muscle in men and women.

However, in order to be effective, the perineal reeducation sessions must be performed regularly in the premises of an experienced practitioner, for example a physiotherapist, which can be particularly restrictive. In addition, the results that are achieved are not always satisfactory.

Therefore, many patients with urinary leakage are obliged to wear specific protections, which are adaptable depending on the needs of patients and the importance of the leaks, such as wipes, diapers or disposable or reusable panties.

However, these devices do not permit to prevent the leaks and, in addition to the discomfort they provide, the wearing of these protections can be felt as particularly troublesome or degrading.

In order to cope therewith, it has been devised to implant strips of synthetic tissue under the urethra for the purpose of supporting it, said strips being attached to the tissues or structures of the abdominal wall or the retropubic space.

However, this solution has the drawback of requiring a surgical procedure and, hence, a hospitalization. In addition, in the medium or long term, the strips would lose their effectiveness, causing a return of the urinary incontinence or, what is even more serious, leading to a retention by fibrosis of the urethra.

As a result, the persons suffering from incontinence are finally obliged to return to the above-mentioned devices for protecting against leakage.

Therefore and to summarize, once the diagnosis of stress urinary incontinence has been established by a specialist, the solutions that are currently provided do not permit to cope in a simple, satisfactory and lasting way with the problems of the urinary leakage.

BRIEF SUMMARY OF THE INVENTION

The invention provides the possibility of coping with the various drawbacks of the state of the art by providing an autonomous and endo-cavitary device intended to be inserted for example into the vagina or into the rectum and permitting to send an appropriate stimulation, in a timely manner, in order to generate a contraction of the perineal muscles, thus avoiding a loss of urine fluid.

To this end, the present invention relates to a probe device for managing incontinence under stress, said probe being capable of being inserted into the vaginal cavity or in the rectal cavity of a person.

Said probe device of the invention is characterized in that it includes at least one autonomous electric power supplying means supplying, on the one hand, at least one means for measuring the variation of a parameter resulting from a physical effort and, on the other hand, at least one means for electrically stimulating the muscles into contact with at least one muscle capable of maintaining urinary continence, said electrical stimulation means being triggered in the event of variation of said parameter.

In particular, the stimulation means is into direct contact, or through the vaginal or rectal mucosa, with the at least one muscle.

Advantageously, said measuring means consists of a pressure sensor capable of measuring a variation of the pressure within said cavity.

In another embodiment of the invention, said measuring means consists of an electrode for measuring an electromyographic signal of the perineal muscles.

Preferably, said electrical muscle stimulation means consists of at least one electrode.

Said electrode is, in a particularly advantageous manner, into contact with the perineal muscles and is capable of generating a contraction of said muscles.

The present invention has many advantages. On the one hand, it can be permanently carried very discretely by the person in order to avoid the loss of urine, without any risk of leaks or bad smells. As a result, the device according to the invention is particularly hygienic. Therefore, the probe device of the invention permits to replace the wearing of diapers, and to avoid a surgical procedure or constraining sessions of perineal reeducation with often random results. Finally, the present device can be worn by a man as well as by a woman.

Further features and advantages of the invention will become clear from the following detailed description of the non-restrictive embodiments of the invention, with reference to the single attached FIGURE schematically representing a probe device according to the invention.

BRIEF DESCRIPTION OF THE SEVERAL VIEWS OF THE DRAWINGS

The understanding of this description will be facilitated when referring to the attached drawings.

The FIGURE is a schematic view of the probe device of the present invention.

DETAILED DESCRIPTION OF THE INVENTION

As shown in the FIGURE, the present invention relates to a probe device 1, which, after insertion into the vaginal cavity or into the rectal cavity of a patient suffering from urinary incontinence under stress, permits to manage this incontinence.

In a particularly advantageous manner, this probe device 1 according to the invention is autonomous. In other words, said device 1 includes at least one autonomous power supply means, for example a battery or a button cell.

This supply means permits to cause the various components of said probe device 1 of the invention to operate.

Indeed and preferably, said device 1 includes, on the one hand, at least one means for measuring 2 a parameter, which results from a physical effort made by the person carrying said device 1 and, on the other hand, at least one means for an electrical muscle stimulation 3. The latter is into contact with at least one muscle capable of maintaining the urinary continence and permits to stimulate this muscle when a physical effort is detected.

In particular, the stimulation means 3 is into direct contact, or through the vaginal or rectal mucosa, with the at least one muscle.

The probe device 1 according to the invention is particularly interesting because it permits to manage the urinary incontinence in a person, man or woman, when a situation of effort is detected by said device 1.

The stress urinary incontinence results namely from a weakening of the muscles of the perineum (or muscles of the pelvic floor, or pelvic muscles) and/or the muscle ensuring the closing of the bladder, the urethral sphincter.

Indeed, these muscles, when they operate normally, permit to withstand an increase in abdominal pressure, due to a situation of effort, such as coughing, laughing, sneezing, or a physical exercise. More specifically, a contraction of the perineal muscles during an effort reinforces the urethral closing pressure also ensured by the sphincter and results namely into maintaining the urethra in the closed position.

In the event of a decrease in the tone of the perineal muscles, the urinary sphincter alone cannot ensure a closing pressure necessary for the continence. As a result, when the pressure increases in the abdominal cavity as a result of an effort, this pressure affects the bladder and urine leakage can occur.

The people affected by urinary incontinence are mostly women, regardless of their age. In some cases, an obstetric trauma may be the cause of a lack of urinary sphincter tone as well as a relaxation of the muscles of the pelvic floor.

However, men can also experience urinary incontinence, in particular when they have been subjected to a total or partial removal of the prostate, or prostatectomy. Indeed, during the operation, it is possible that the urethral sphincter and/or its innervation is (are) accidentally affected, making said sphincter less effective.

Therefore, the probe device 1 according to the invention is likely to be used by both men and women.

In a first embodiment of the probe device 1 of the invention, the means for measuring 2 a parameter resulting from a physical effort when the parameter is a variation in pressure, is at least one pressure sensor, the latter being capable of measuring a variation, namely an increase in pressure, within a body cavity, such as the vaginal or rectal cavity.

This increase in pressure in the vaginal or rectal cavity results from an increase in pressure in the abdomen, which is in turn caused by a situation of effort.

The detection of an increase in pressure in the cavity by said measuring means 2 permits to trigger the electrical stimulation means 3 of the device 1 positioned into contact with at least one muscle ensuring the urinary continence, preferably a perineal muscle. The electrical stimulation of said muscle causes electro-induced contraction of the latter, resulting into urinary continence.

In particular, the stimulation means is into direct contact, or through the vaginal or rectal mucosa, with said at least one muscle. Thus, the stimulation can be done directly on the muscle ensuring the urinary continence or indirectly via said mucosa.

Preferably, the means for measuring the pressure includes a balloon 4, which is placed into contact with the vaginal mucosa or the anal mucosa, in order to detect the variations in pressure in the abdominal cavity. To this end, the balloon 4 is associated with at least one pressure sensor located inside the balloon 4 and/or at least one contact lamella of deformable material, positioned on the surface of said balloon 4.

Therefore, by applying the probe device 1 according to the invention, urinary leakage is avoided.

In particular, the balloon 4 is placed at one end of the probe. More particularly, said end is intended to be inserted until it is into contact with the cervix or beyond the anal canal.

The embodiment of the device 1 described above permits to avoid the stress urinary incontinence when the muscles, in particular the perineal muscles, no longer show any activity. In this case, as indicated, the parameter resulting from an effort being measured is the variation in pressure, as described above.

However, it is also conceivable that the person suffering from stress urinary incontinence still has a weak contraction of the perineal muscles, but insufficient to avoid a loss of urine fluid.

In this case, corresponding to the second embodiment of the probe device 1 according to the invention, the means for measuring 2 the variation of a parameter resulting from a physical effort consists of a bipolar electrode for measuring an electro-myographic signal from at least one perineal muscle, not shown in the attached FIGURE.

In other words, the parameter being measured here consists of an electric current accompanying the weak but existing muscular activity, namely of the perineum, this activity resulting from a physical effort.

In this particular embodiment, the stimulation means, preferably also a bipolar electrode into contact with the perineal muscles, will permit, through an electro-induced stimulation, to amplify the existing muscular activity and thus to cause a sufficient contraction of the muscle in order to maintain urinary continence.

The probe device 1 according to the invention thus permits, in a particularly advantageous way, to manage the stress urinary incontinence both in patients capable of producing a weak perineal muscle contraction and in patients whose perineum no longer shows any activity.

In an advantageous embodiment, the probe device 1 of the invention includes both a means for measuring the variation in pressure and a bipolar electrode for measuring an electro-myographic signal detecting an electrical activity of the perineal muscles.

In addition, it is also conceivable to calibrate the level of pressure or of intensity of the electro-myographic signal resulting into the triggering of the electrical stimulation means 3, in order to adapt the device 1 to the level of incontinence of the patient.

As regards now said electrical stimulation means 3 of the probe device 1, positioned into contact with at least one muscle capable of maintaining the continence, the latter advantageously includes two stimulation electrodes 31, 32.

During an increase in abdominal pressure, the means for measuring said pressure activates the means 3 for an electrical muscle stimulation of the perineal muscles. Should the case arise, each electrical muscle stimulation as an intensity and the slope or rate of creation of this stimulation, which are proportional to a rate of creation and to a level of pressure, when the parameter is a variation in pressure and when the variation in pressure is an increase in pressure.

Since the electrodes 31 and 32 are placed at the level of the deep muscular planes of the perineum, the so created stimulation causes, via these electrodes 31 and 32, the contraction of said perineum and increases the urethral closing pressure.

In addition, the sensor that activates the electro-induced contraction is adjustable and permits to activate said stimulation at a predetermined pressure threshold below the pressure threshold from which the leak occurs, wherein the variation in pressure is a pressure below the predetermined pressure threshold.

More generally, the device comprises the balloon 4 at one end, and at least one electrode (a second stimulation electrode 32) in front of the balloon 4, then preferably the other electrode (a first stimulation electrode 31) in front of the second stimulation electrode 32. The positions of the electrodes 31 and 32 are adapted to the stimulation of said at least one muscle.

Preferably, as shown in the attached FIG. 1, the probe device 1 according to the invention is comprised of a first portion formed by a cylindrical tube 5 including a tube body 5A having a periphery 5B, and at one of its ends, a means for manually gripping 6 said device 1 and, at the opposite end, a second substantially spherical portion 7.

This spherical portion 7 advantageously comprises the balloon 4 with, on its surface, at least one pressure sensor and/or at least one contact lamella of deformable material. Preferably, the balloon 4 is inflatable by a suitable means that can form the gripping means 6. The inflation means can be a pump. Preferably, the pressure sensor is temperature compensated.

A first stimulation electrode 31 can be positioned on the periphery of the cylindrical tube 5.

As regards the second stimulation electrode 32, it is preferably positioned at the periphery of the spherical portion 7 of the probe device 1 according to the invention.

The probe device 1 according to the invention permits to manage and to avoid the urinary incontinence permanently, while avoiding the drawbacks associated with the currently provided solutions of the state of the art.

Therefore, the user of the present device 1 will be completely autonomous, and will no longer be subject to urinary leakage.

Indeed, in a timely manner the device 1 will cause an electrical stimulation of the perineal muscles, generating an electro-induced contraction of the latter. It is thus understood that by means of the present device untimely stimulation of the perineal muscles is avoided.

In addition, thanks to this probe device 1, as electrical stimulation of the muscles occurs, it is conceivable that the locking reflex and the myotatic reflex of the perineum become functional again.

I claim:

1. A probe device for inserting into a body cavity, said probe device comprising:
    a cylindrical tube being comprised of tube body with a periphery, said cylindrical tube having means for manually gripping at one end and a spherical portion at an opposite end;
    at least one autonomous electric power supplying means;
    at least one means for measuring a parameter resulting from a physical effort, wherein said parameter is a variation in pressure; and
    at least one means for producing and delivering an electrical muscle stimulation in communication with said at least one means for measuring, wherein said electrical muscle stimulation has an intensity and a slope of creation of the stimulation, wherein said intensity and said slope of creation of the stimulation are proportional to a rate of creation and a level of said variation in pressure, said variation in pressure being an increase in pressure, wherein the means for measuring is further comprised of a spherical balloon adjacent said spherical portion, wherein said at least one means for an electrical muscle stimulation includes a first stimulation electrode on said periphery of said tube body and a second stimulation electrode positioned at said spherical portion and between said balloon and said first stimulation electrode so as to stimulate in more than one muscular plane.

2. The probe device according to claim 1, wherein the means for measuring is further comprised of a sensor.

3. The probe device according to claim 2, wherein said sensor is comprised of a pressure sensor located inside said balloon.

4. The probe device according to claim 2, wherein the means for measuring is further comprised of a contact lamella on a surface of said balloon, said contact lamella being comprised of deformable material.

5. The probe device according to claim 1, wherein said variation in pressure is a pressure increase amount below a predetermined pressure threshold.

6. The probe device according to claim 1, further comprising:

a means for measuring an electrical activity on said probe, said means for measuring being an electrode for bipolar signals.

* * * * *